(12) United States Patent
Korendovych

(10) Patent No.: US 10,695,399 B2
(45) Date of Patent: Jun. 30, 2020

(54) PEPTIDES FOR PREVENTION OF HIV INFECTION

(71) Applicant: Ivan V. Korendovych, Syracuse, NY (US)

(72) Inventor: Ivan V. Korendovych, Syracuse, NY (US)

(73) Assignee: SYRACUSE UNIVERSITY, Syracuse, NY (US)

( * ) Notice: Subject to any disclaimer, the term of this patent is extended or adjusted under 35 U.S.C. 154(b) by 0 days.

(21) Appl. No.: 16/671,610

(22) Filed: Nov. 1, 2019

(65) Prior Publication Data

US 2020/0054710 A1   Feb. 20, 2020

Related U.S. Application Data

(62) Division of application No. 16/047,490, filed on Jul. 27, 2018, now Pat. No. 10,512,666.

(60) Provisional application No. 62/539,774, filed on Aug. 1, 2017.

(51) Int. Cl.
  *A61K 38/10* (2006.01)
  *A61K 9/00* (2006.01)
  *A61K 38/16* (2006.01)

(52) U.S. Cl.
  CPC ............ *A61K 38/10* (2013.01); *A61K 9/0014* (2013.01); *A61K 38/16* (2013.01); *A61K 9/0034* (2013.01)

(58) Field of Classification Search
  None
  See application file for complete search history.

(56) References Cited

U.S. PATENT DOCUMENTS 5,585,353 A * 12/1996 Merrifield ........ C07K 14/43563
                                                514/2.4
2012/0237501 A1 * 9/2012 Wang .................... A61K 38/04
                                                424/130.1

* cited by examiner

*Primary Examiner* — Maury A Audet
(74) *Attorney, Agent, or Firm* — Bond Schoeneck & King, PLLC; David Nocilly; George McGuire

(57) ABSTRACT

Two peptides that can selectively bind to SEVI and block the enhanced infectivity that results from the interaction of SEVI with HIV. The two peptides comprise the amino acid sequences FEEIVQEIEDFLENLV (SEQ. ID NO: 1) and GIGAVLEVLTTGLPALISWIEEEEQQ (SEQ. ID. NO: 2). The peptides may be administered topically, either alone or in combination with other prophylactics, agents, etc.

5 Claims, 4 Drawing Sheets

Specification includes a Sequence Listing.

FEEIVQEIEDFLENLV is SEQ. ID NO: 1

FEEIVQEIEDFLENLV is SEQ. ID NO: 1

E-melittin is GIGAVLEVLTTGLPALISWIEEEEQQ (SEQ. ID. NO:2)

PEPTIDES FOR PREVENTION OF HIV INFECTION

CROSS-REFERENCE TO RELATED APPLICATIONS

The present application is a divisional of U.S. application Ser. No. 16/047,490, filed on Jul. 27, 2018, which claims priority to U.S. Provisional App. No. 62/539,774, filed on Aug. 1, 2017.

BACKGROUND OF THE INVENTION

1. Field of the Invention

The present invention relates to the prevention of human immunodeficiency virus (HIV) infections and, more particularly, to compounds that will block human semen proteins from increasing the infectivity of HIV.

2. Description of the Related Art

Human semen contains proteins that form amyloid fibrils referred to as semen enhancer of virus infection (SEVI), that have been recently shown to dramatically increase (400,000-fold) the infectivity of human immunodeficiency virus (HIV) in vitro. As a result, inhibiting the interaction of SEVI with HIV virus presents an essentially untapped strategy for preventing or reducing the risk of an HIV infection.

Conventional approaches to addressing the impact of SEVI on the likelihood of an HIV infection include the development molecules that will bind to SEVI and inhibit the interaction with HIV or include an anti-viral component. For example, the amyloid-β binding molecule, BTA-EG$_6$ that can binds SEVI-fibrils has been combined with anti-viral agents to disrupts the enhanced infectivity of HIV. Other compounds, such as gallic acid, have been proposed for use in inhibiting semen-mediated enhancement of HIV infection and suggest the potential utility of incorporating gallic acid into a multi-component microbicide targeting both the HIV virus and host components that promote viral infection. While these approaches may prove to be effective, there continues to be a need in the art for an approach that can inhibit the interaction of SEVI with HIV virus and thus reduce the risk of infection.

BRIEF SUMMARY OF THE INVENTION

The present invention comprises to proteins that can successfully bind to SEVI and block the enhanced infectivity that results from the interaction of SEVI with HIV. The two proteins comprise the amino acid sequence FEEIVQEIEDFLENLV (SEQ. ID NO: 1), referred to herein as Peptide 1, and the amino acid sequence GIGAVLEVLTTGLPALISWIEEEEQQ (SEQ. ID. NO: 2), referred to as Peptide 2. The C-termini may be amidated and the N-termini are either free or acetylated, or attached to a fluorescence dye for the purposes of binding studies.

Binding studies establish that these proteins do not bind to the non-aggregated portion of the human protein prostatic acid phosphatase (PAP) that does not promote infectivity, but the proteins do bind to SEVI, the aggregated portion of the human protein that does promote infectivity. Thus, the proteins according to the present invention are selective for the aggregated state that is believed to be implicated in increased infectivity and offer an avenue for use in reducing HIV infections.

In an embodiment, the present invention is a compound for reducing HIV infectivity, comprising an artificial peptide sequence that binds to an aggregated semen enhancer of virus infection (SEVI) but does not bind to a non-aggregated portion of the human protein prostatic acid phosphatase (PAP). The artificial peptide sequence may be SEQ ID NO: 1 and combined with a topical agent or applied to a prophylactic. The artificial peptide sequence may also be SEQ ID NO: 2 and combined with a topical agent or applied to a prophylactic.

In another embodiment, the present invention may be a combination product for reducing HIV infectivity, comprising a first artificial peptide sequence that binds to an aggregated semen enhancer of virus infection (SEVI) but does not bind to a non-aggregated portion of the human protein prostatic acid phosphatase (PAP) combined with a second artificial peptide sequence that binds to SEVI but does not bind to a non-aggregated portion of PAP. The first artificial peptide sequence may be SEQ ID NO: 1 and the second artificial sequence may be SEQ ID NO: 2. The first artificial peptide sequence and the second artificial sequence may be combined with a topical agent or applied to a prophylactic.

In a further embodiment, the present invention may be a method of reducing the likelihood of an HIV infection, comprising the step of applying an artificial peptide sequence that binds to an aggregated semen enhancer of virus infection (SEVI) but does not bind to a non-aggregated portion of the human protein prostatic acid phosphatase (PAP) to a subject at risk of an HIV infection. the artificial peptide sequence comprises SEQ ID NO: 1. The artificial peptide sequence may be SEQ ID NO: 1 and combined with a topical agent or applied to a prophylactic. The artificial peptide sequence may also be SEQ ID NO: 2 and combined with a topical agent or applied to a prophylactic. The method may also comprise applying a combination of a first artificial peptide sequence that is SEQ ID NO: 1 and a second artificial sequence that is SEQ ID NO: 2 either topically or in combination with a prophylactic.

BRIEF DESCRIPTION OF THE SEVERAL VIEWS OF THE DRAWING(S)

The present invention will be more fully understood and appreciated by reading the following Detailed Description in conjunction with the accompanying drawings, in which.

DETAILED DESCRIPTION OF THE INVENTION

The present invention comprises two novel peptides and the use of those peptides to reduce the risk of an HIV infection. Peptide 1 has the sequence FEEIVQEIEDFLENLV (SEQ. ID NO: 1) and Peptide 2 has the sequence GIGAVLEVLTTGLPALISWIEEEEQQ (SEQ. ID NO: 2). The C-termini of Peptide 1 and Peptide 2 are amidated, and the N-termini of Peptide 1 and Peptide 2 may be free or acetylated. For the purposes of testing efficacy the N-termini of Peptide 1 and Peptide 2 may be attached to a fluorescence dye.

Figure 1A:
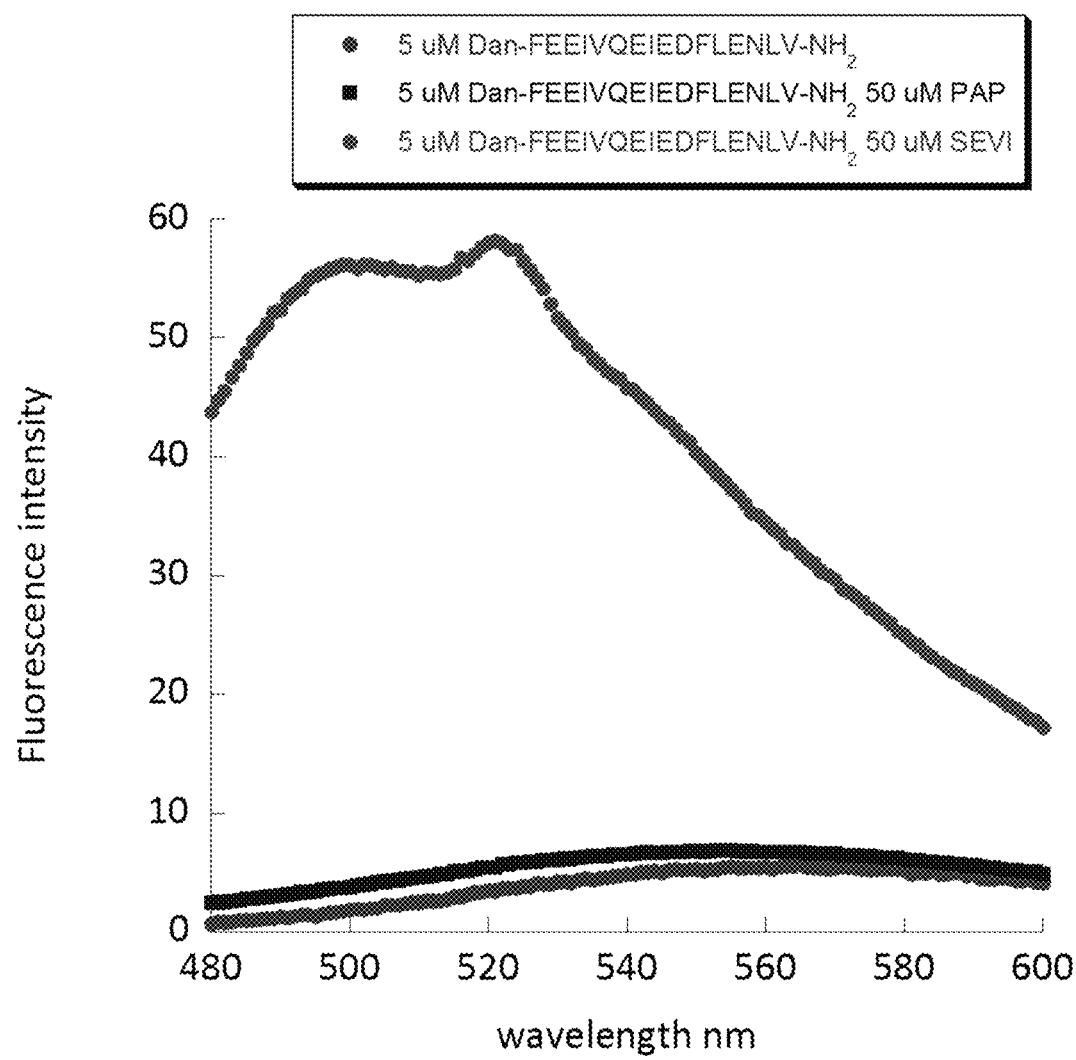
FIG. 1A is a graph of fluorescence spectra of a first dansylated peptide according to the present invention in a binding study with PAP and SEVI at a first concentration.
Figure 1B:
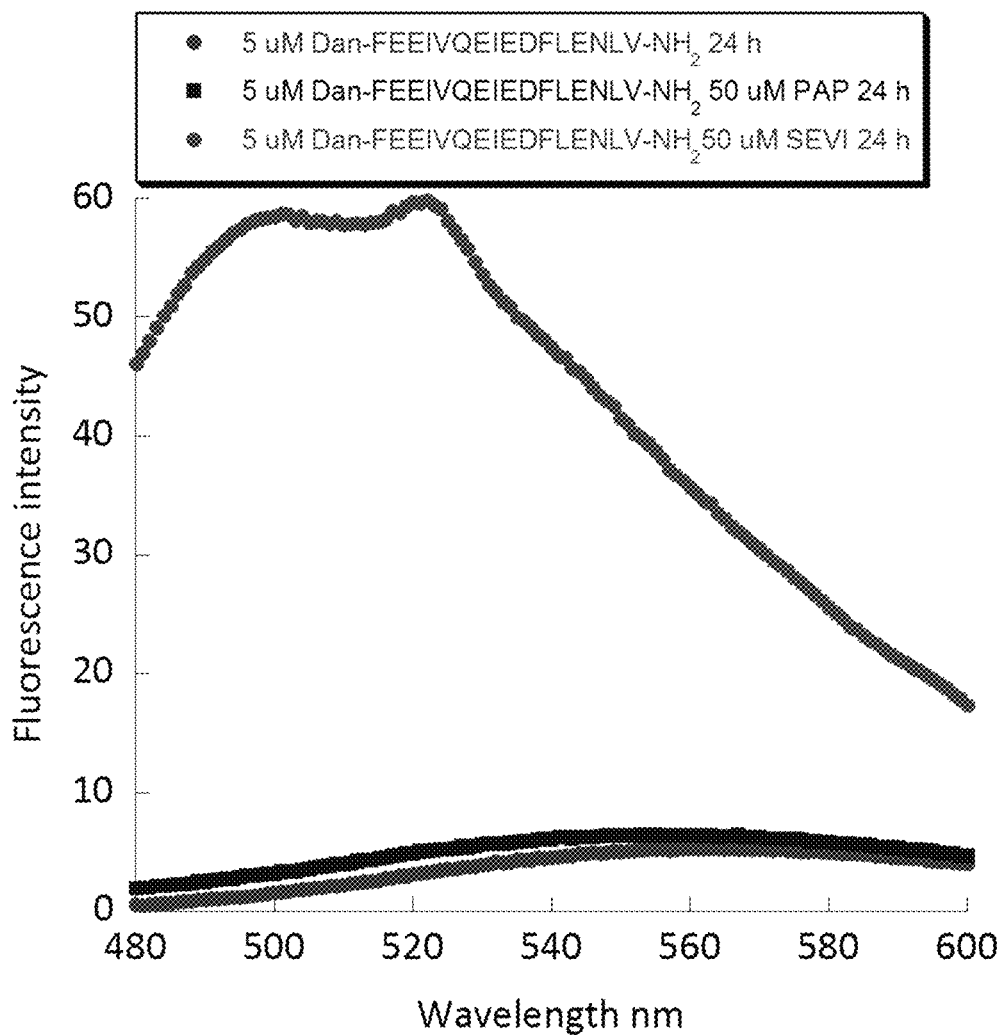
FIG. 1B is a graph of fluorescence spectra of the first dansylated peptide according to the present invention in a binding study with PAP and SEVI at a first concentration incubated for 24 hours.
Figure 2A:
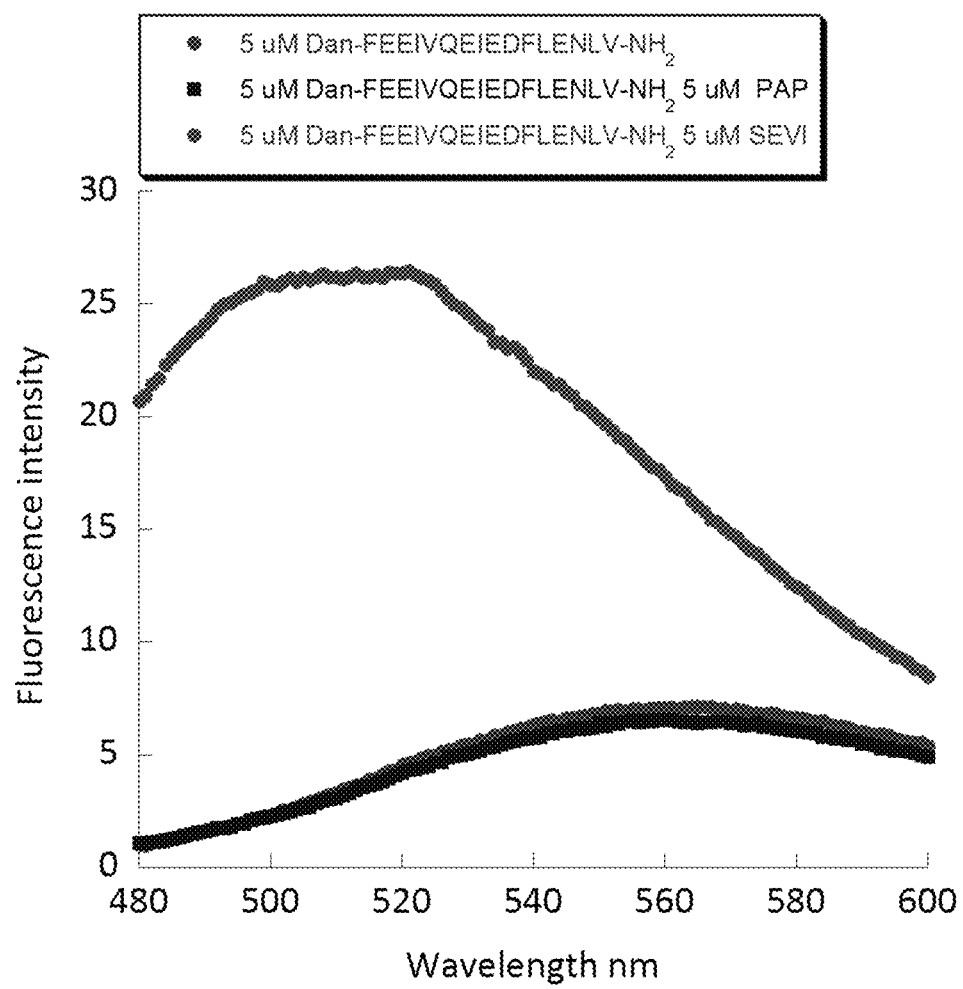
FIG. 2A is a graph of fluorescence spectra of a first dansylated peptide according to the present invention in a binding study with PAP and SEVI at a second concentration.

Based on fluorescence binding data, as seen in FIGS. 1A, 1B, and 2A, Peptide 1 binds to SEVI (with an effective Kd of less than 5 micromolar), but not to non-aggregated peptides derived from the precursor protein PAP. PAP is the non-aggregated portion of the human protein that does not promote infectivity, while SEVI is the aggregated portion of the human protein that promotes infectivity. Dansyl is the fluorescent dye that is attached to peptides. A change in Dansyl fluorescence indicates change in the environment, i.e. binding. The physiological concentration of PAP and SEVI is 5 micromolar.

Figure 2B:
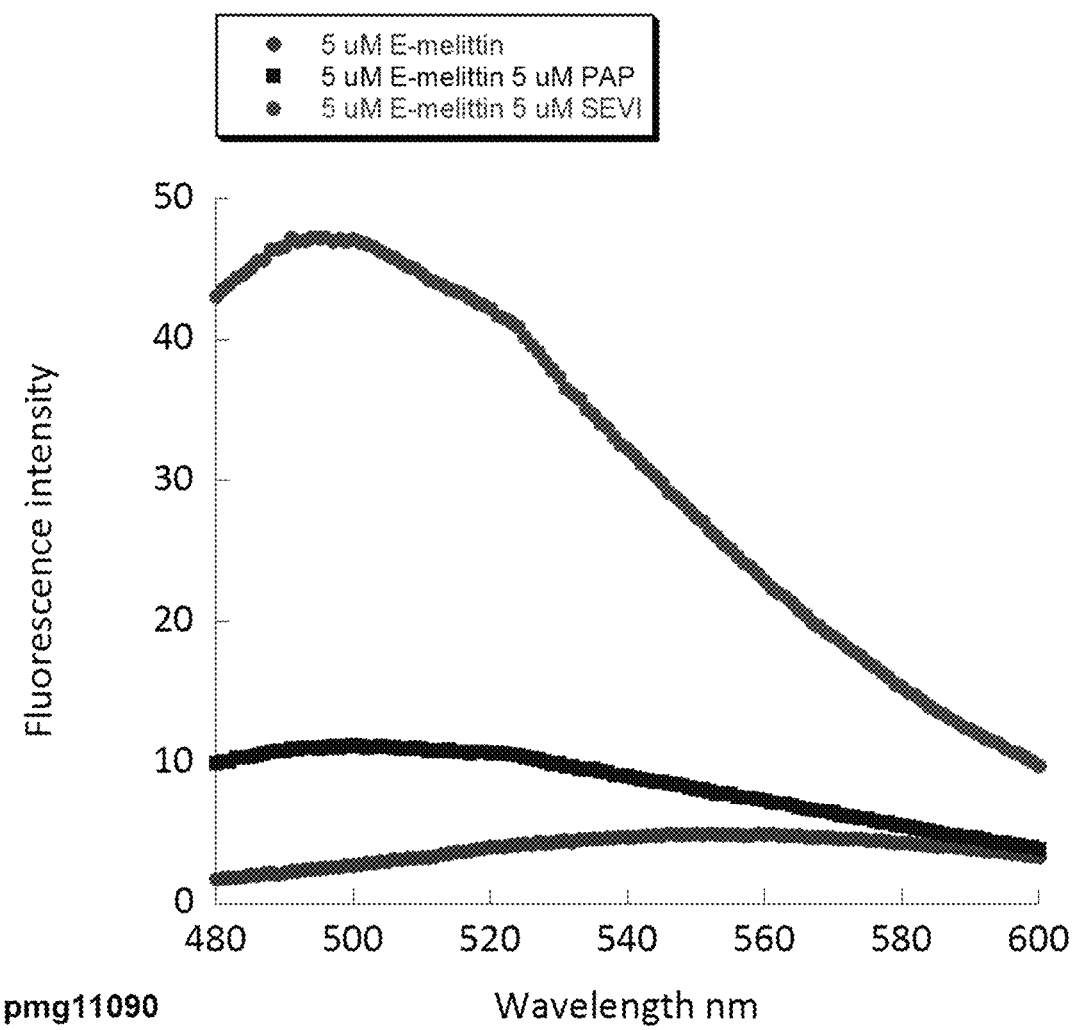
FIG. 2B is a graph of fluorescence spectra of a second dansylated peptide according to the present invention in a binding study with PAP and SEVI at a second concentration.

As seen in FIG. 2B, Peptide 2 binds to both aggregated SEVI (with higher affinity) and not to the non-aggregated peptides derived from the precursor protein.

As the binding of conventional molecules to SEVI leads to decreased HIV infectivity, it should be understood by those of skill in the art that Peptide 1 and Peptide 2 are efficient therapeutics for the prevention of HIV infections. Preferably, Peptide 1 and Peptide 2 are applied topically, either directly or in combination with prophylactics. The present invention offers advantages over conventional therapeutics due to the ease of preparation, evolvability (phage display will be used to further increase affinity and selectivity as necessary), cost, and lack of immunogenicity as Peptide 1 and Peptide 2 are derived from naturally occurring antimicrobial peptides. Preliminary studies additionally show that Peptide 1 and Peptide 2 are non-toxic.

An effective amount of Peptide 1 and Peptide 2 can be administered to or by an individual in need of treatment. Thus, the present invention includes the method of preventing a sexually transmitted infection in a subject by the administration of Peptide 1, Peptide 2, or combinations thereof. Administering Peptide 1 and Peptide 2 binds to SEVI or SEVI-fibrils and thus interferes with the ability of the SEVI-fibrils to enhance an HIV infection. Effective amounts of Peptide 1 and Peptide 2 are any amounts that induce the desired response while not inducing unacceptable toxicity in a subject. Additionally, the corresponding enantiomers (i.e. peptides having the same sequences but made of the D-amino acids) can be used to increase proteolytic stabilities in various formulations.

Peptide 1 and Peptide 2 should be fully compatible with currently used spermicidal and vaginal creams as well as lubricants and moisturizers and thus can be used in combination therewith or provided on their own. The appropriate formulations can be applied directly and/or indirectly (e.g. through use of condoms) as well as used in combination with pharmaceuticals used to treat other conditions. For example, acceptable formulations foams, gels, creams, lotions, and lubricants may include lactic acid, methylparaben, povidone, propylene glycol, purified water, sodium carboxymethylcellulose, sorbic acid, sorbitol, benzoic acid, cellulose gum, cetyl alcohol, fragrance, glacial acetic acid, methylparaben, phosphoric acid, polyvinyl alcohol, propellants, purified water, stearamidoethyl diethylamine, glycerin, Nonoxynol-9, parabens, chlorhexidine gluconateand/or stearic acid. Topical formulations will preferably contain between about 1 and 10 mg of peptides per 1 mL of topical agent, but may have lower of higher amounts subject to efficacy and toxicity studies. It should be recognized that concentrations may also be adjusted to compensate for the particular active and inactive ingredients used along with Peptide 1 and Peptide 2.

What is claimed is:

1. A method of reducing the risk of infectivity by human immunodeficiency virus (HIV), comprising the step of applying an artificial peptide sequence that binds to an aggregated semen enhancer of virus infection (SEVI) amyloid fibrils of prostatic acid phosphatase (PAP) but does not bind to non-aggregated PAP to a subject in need thereof and at risk of HIV infection by sexual transmission, wherein the artificial peptide sequence is selected from the group consisting of SEQ ID NO: 1 and SEQ ID NO: 2.

2. The method of claim 1, wherein the step of applying the artificial peptide sequence comprises applying the artificial peptide sequence topically.

3. The method of claim 1, wherein the step of applying the artificial peptide sequence comprises applying the artificial peptide sequence to a prophylactic.

4. The method of claim 1, wherein the step of applying the artificial peptide sequence comprises the step of applying a first artificial peptide sequence that is SEQ ID NO: 1 and the step of applying a second artificial peptide sequence that is SEQ ID NO: 2.

5. The method of claim 4, wherein the step of applying the artificial peptide sequence comprises applying the first artificial peptide sequence and the second artificial sequence topically or in combination with a prophylactic.

* * * * *

SEQUENCE LISTING

```
<160> NUMBER OF SEQ ID NOS: 2

<210> SEQ ID NO 1
<211> LENGTH: 16
<212> TYPE: PRT
<213> ORGANISM: Artificial Sequence
<220> FEATURE:
<223> OTHER INFORMATION: binding protein for semen enhancer of virus
      infection (SEVI)

<400> SEQUENCE: 1

Phe Glu Glu Ile Val Gln Glu Ile Glu Asp Phe Leu Glu Asn Leu Val
1               5                   10                  15

<210> SEQ ID NO 2
<211> LENGTH: 26
<212> TYPE: PRT
<213> ORGANISM: Artificial Sequence
<220> FEATURE:
<223> OTHER INFORMATION: binding protein for semen enhancer of virus
      infection (SEVI)

<400> SEQUENCE: 2

Gly Ile Gly Ala Val Leu Glu Val Leu Thr Thr Gly Leu Pro Ala Leu
1               5                   10                  15

Ile Ser Trp Ile Glu Glu Glu Gln Gln
            20                  25
```